United States Patent [19]

Sebek et al.

[11] 4,304,855

[45] Dec. 8, 1981

[54] ALLYLIC METHYL-HYDROXYLATED NOVOBIOCINS

[75] Inventors: Oldrich K. Sebek, Kalamazoo; Lester A. Dolak, Cooper Township Kalamazoo County, both of Mich.

[73] Assignee: The Upjohn Company, Kalamazoo, Mich.

[21] Appl. No.: 793,784

[22] Filed: May 5, 1977

[51] Int. Cl.³ .............................................. C12P 19/60
[52] U.S. Cl. ..................................... 435/75; 435/125; 435/253; 435/822
[58] Field of Search .................. 260/343.3 R; 435/75, 435/123, 125, 253, 822; 536/13

[56] References Cited

U.S. PATENT DOCUMENTS

| | | | |
|---|---|---|---|
| 3,049,534 | 8/1962 | Wallick | 536/13 |
| 3,175,944 | 3/1965 | Hoeksema | 536/13 |
| 3,652,536 | 3/1972 | Sebek et al. | 536/13 |
| 3,654,536 | 3/1972 | Sebek et al. | 536/13 |
| 3,890,297 | 6/1975 | Dolak | 536/13 |
| 4,128,563 | 12/1978 | Sebek et al. | 435/125 |
| 4,147,704 | 4/1979 | Dolak | 435/125 |
| 4,148,992 | 4/1979 | Sebek et al. | 435/75 |

*Primary Examiner*—Peter A. Hruskoci
*Attorney, Agent, or Firm*—Bruce Stein

[57] ABSTRACT

The present invention relates to a fermentation process for producing allylic methyl-hydroxylated novobiocin and derivatives thereof.

8 Claims, No Drawings

ALLYLIC METHYL-HYDROXYLATED NOVOBIOCINS

BACKGROUND OF THE INVENTION

Novobiocin is an antibiotic useful in the treatment of staphylococcal infections and in urinary tract infections caused by certain strains of Proteus. It shows no cross resistance with penicillin and is active against penicillin-resistant strains of Staphylococcus aureus. Novobiocin is produced through fermentation by streptomycetes. The methods for production, recovery and purification of novobiocin are described in U.S. Pat. No. 3,049,534.

Dihydronovobiocin is an antibiotic prepared by hydrogenating novobiocin according to the procedures disclosed in U.S. Pat. No. 3,175,944.

As with any antibiotic it is always highly advantageous to prepare derivatives or analogs since these often lead to new antibiotics with increased potency, fewer and less severe side effects, and/or a different spectrum of antibiotic activity. In 1972 U.S. Pat. No. 3,652,536 disclosed an enzymatic process for cleaving novobiocin to produce novenamine. U.S. Pat. No. 3,890,297 disclosed a selective process for N-acylation of novenamine which produces novobiocin analogs which have antibacterial activity.

The following patents disclose modifications of novobiocin: U.S. Pat. Nos. 2,925,411; 2,938,899; 2,945,064; 3,049,550; and 3,445,455; British Pat. Nos. 856,816 and 997,179; and German Pat. Nos. 1,088,982 and 1,076,144.

However none of the above relate to modification of the isopentenyl side chain on the benzamide ring. To our knowledge only the combined process of U.S. Pat. Nos. 3,652,536 and 3,890,297 disclosed a useful method for producing such analogs until the present invention.

SUMMARY OF THE INVENTION

Disclosed s a hydroxynovobiocin-type compound of the formula:

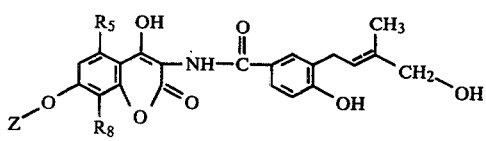

or pharmaceutically acceptable salt thereof, where $R_5$, $R_8$, Z and ═══ are defined below.

Also disclosed is a process for preparing a hydroxynovobiocin-type compound of formula:

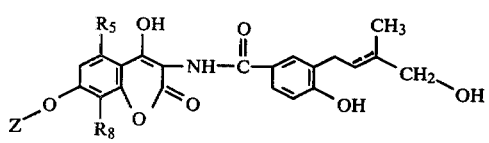

which comprises (1) cultivating Sebekia benihana having the identifying characteristics of NRRL 11,111 and novobiocinhydroxylating mutants thereof in an aqueous nutrient medium under aerobic conditions;

(2) contacting a novobiocin-type compound of the formula:

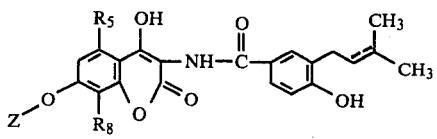

with the Sebekia benihana culture and;

(3) recovering the hydroxynovobiocin-type compound (II) where $R_5$, $R_8$, Z and ═══ are defined below.

The definitions and explanations below are for the terms as used throughout the entire patent application including both the specification and claims.

$R_5$ and $R_8$ may be the same or different and are hydrogen, alkyl of from 1 thru 5 carbon atoms, alkenyl of from 1 thru 5 carbon atoms, halogen, nitro, cyano, carboxyl, or $-NR_\alpha R_\beta$.

$R_\alpha$ and $R_\beta$ may be the same or different and are hydrogen or alkyl of 1 thru 5 carbon atoms.

Alkyl of 1 thru 5 carbon atoms includes, for example, methyl, ethyl, propyl, butyl, pentyl and isomers thereof.

Alkenyl of 1 thru 5 carbon atoms includes, for example, propenyl, 2-butenyl, 3-pentenyl and isomers thereof.

Halogen includes, for example, fluorine, chlorine, bromine and iodine atoms.

═══ is a single or double bond.

Z is hydrogen or

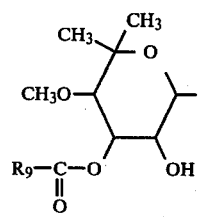

where R is amino, 2-pyrryl, 2-(5-methyl)-pyrryl, 2-furyl, and 2-(5-methyl)-furyl.

The lyxoside formula does not designate any particular stereochemical relationship.

Pharmaceutically acceptable refers to those properties and/or substances which are acceptable to the patient from a pharmacological-toxicological point of view and to the manufacturing phrmaceutical chemist from a physical-chemical point of view regarding composition, formulation, stability, patient acceptance and bioavailability.

All temperatures are in degrees Centigrade.

TLC refers to thin layer chromatography.

SSB refers to a mixture of isomeric hexanes.

Brine refers to an aqueous saturated sodium chloride solution.

Dicalite ® 4200 refers to diatomaceous earth as marketed by Grefco, Inc., Los Angeles, California, U.S.A.

TYG refers to a growth medium containing tryptone, yeast extract and glucose.

UCON ® refers to a mixture of polypropylene glycol and polyethylene glycol as marketed by Union Carbide, Park Avenue, New York, N.Y., U.S.A.

IR refers to infrared spectroscopy.

UV refers to ultraviolet spectroscopy.

NMR refers to nuclear magnetic resonance spectroscopy.

When solvent pairs are used, the ratio of solvents are all given as volume/volume (v/v).

Contacting refers to (1) the addition of a novobiocin-type compound (I) to a growing culture of *Sebekia benihana* or (2) the addition of a growing culture of *Sebekia benihana* to a fermentation which has produced a novobiocin-type compound (I)

DETAILED DESCRIPTION OF THE INVENTION

The microorganism of this invention was studied and characterized by Alma Dietz and Grace P. Li of the Upjohn Research Laboratories.

An unusual actinomycete, isolated from a soil sample was found to have characteristics by which it coud be differentiated from described genera of actinomycetes.

Organisms characterized as actinomycetes are placed in Part 17. Actinomycetes and Related Organisms in the eighth edition of Bergey's Manual (Gottlieb, D., 1974. Order 1. Actinomycetales Buchanan 1917, pp. 657–659, In R. E. Buchanan and N. E. Gibbons (eds.) Bergey's manual of determinative bacteriology, 8th ed. The Williams & Wilkins Co., Baltimore). The new culture is aerobic to facultatively anaerobic, forms branching filaments, substratal diameter 0.7–0.9 $\mu$m and aerial (0.6 $\mu$m), spores in chains of usually 10 or less and pseudosporangia with smooth and rough spores. The culture belongs to Order 1. Actinomycetales Buchanan 1917.

The new organism has true mycelial filaments that remain intact. Colonies on agar are restricted, raised, and variously convoluted. Aerial mycelium is not abundant. Pseudosporangia are detected by SEM. Spores measure 0.7–1.1$\times$1.3–1.8 $\mu$m. Spores are usually cross ridged. Motility has not been detected.

Other unique properties are a Type III cell wall (meso-DAP). Aspartic acid, glycine, glutamic acid, alanine and two unidentified purple components are also seen in cell wall preparations. A whole cell sugar pattern of mannose and madurose is found.

Whole cell sugar patterns have been suggested as genus characteristic in combination with whole cell wall patterns. This culture might be considered an Actinomadura sp. (Cross, T., and M. Goodfellow, 1973, Taxonomy and classification of the actinomycetes, pp. 11–112. In G. Sykes and F. A. Skinner (ed.), The Actinomycetales: characteristics and practical importance. Academic Press Inc., New York; Lechevalier, M. P., and H. A. Lechevalier, 1970, A critical evaluation of the genera of aerobic actinomycetes, pp. 393–405. In H. Prauser (ed.), The Actinomycetales, Gustav Fisher, Jena; and Prauser, H., 1970, Characters and genera arrangement in the Actinomycetales, pp. 407–418, In H. Prauser (ed.), The Actinomycetales, Gustav Fischer, Jena) based on its cell wall components meso-DAP and madurose. However, its sporangial-like bodies, whole cell pattern, and general cultural characteristics lead us to believe that it is a unique new member of the family Actinoplanaceae (Couch, J. N., 1955, A new genus and family of the Actinomycetales, with a revision of the genus Actinoplanes, J. Elisha Mitchell Sci. Soc. 71:148–155; Couch, J. N. and C. E. Bland, 1974, Family IV, Actinoplanaceae Couch 1955, pp. 716–718, In R. E. Buchanan and N. E. Gibbons (ed.) Bergey's manual of determinative bacteriology, 9th ed., The Williams and Wilkins Co., Baltimore; Lechevalier, H. A. and M. P. Lechevalier, supra; and Prauser, H. supra). We cannot place the culture in any of the described genera of this family. Therefore, we propose the new genus Sebekia of the family Actinoplanaceae. The genus derivation is from the family name of the individual who has investigated the utility of the culture. The species name proposed is benihana. This name, which means red flower, is for the red floret-like growth of the culture.

The description of the new genus and species is based on a single strain. Sebekia is the type genus; *Sebekia behihana* (NRRL 11,111) is the type species. This is in accordance with Section 4. Nomenclatural Types and Their Designation of the Bacteriological Code (International Code of Nomenclature of Bacteria, 1966, Edited by the Editorial Board of the Judicial Commission of the International Committee on Nomenclature of Bacteria, Int. J. Syst. Bacteriol., 16:459–490).

Description

*Sebekia benihana* Dietz and Li, gen. nov., sp. nov.

Color Characteristics. Aerial growth pale pink to pale gray (usually sparse). Melanin negative. Appearance on Ektachrome is given in Table 1. Reference color characteristics are given in Table 2. The culture may be placed in the red color group of Tresner and Backus (Tresner, H. D., and E. J. Backus, 1963, System of color wheels for streptomycete taxonomy, Appl. Microbiol. 11:335–338).

Microscopic Characteristics. Spore chains short (usually less than 10 spores per chain), straight [RF in the sense of Pridham et al. (Pridham, T. G., C. W. Hesseltine, and R. G. Benedict, 1958, A guide for the classification of streptomycetes according to selected groups, Placement of strains in morphological sections, Appl. Microbiol., 6:52–79)]. Spores unusually elongate with a flattened midsection. Spores appear to have tiny spines by direct transmission electron microscope (TEM) examination and cross ridging by TEM examination of carbon replica preparations and direct scanning electron microscope (SEM) examination. The cross ridging is such that an erroneous concept of spines can be obtained from direct TEM which gives only a spore silhouette. The cross ridging appears to come from a twisting sheath which constricts to form spores. Spore chains appear to arise from substrate and aerial hyphae. The terminal spore is frequently bulbous. Spore chains also appear to initiate from a bulbous outgrowth from the aerial or vegetative hyphae. Pseudosporangia appear to be formed from hyphae which come together or "collide". Smooth or rough-surfaced spores are ejected from the sporangia. The observations described are best seen by study of SEM stereopairs.

Micromonospora-like spores appear on the substrate mycelium. No motile spores have been detected.

Growth on Carbon Compounds. Under the test conditions of Pridham and Gottlieb (Pridham, T. G., and D. Gottlieb, 1948, The utilization of carbon compounds by some Actinomycetales as an aid for species determination, J. Bacteriol. 56:101–114), growth was good on the basal medium plus D-xylose, L-arabinose, D-fructose, D-galactose, D-glucose, D-mannose, maltose, lactose, cellobiose, raffinose, dextrin, soluble starch, glycerol, and inositol; moderate on the basal medium plus rhamnose, sucrose, salicin, sodium acetate, and sodium succinate; doubtful on the control (basal medium with no carbon compound added) and on the basal medium with inulin, dulcitol, mannitol, sorbitol, sodium tartrate, and sodium citrate. There was no growth on the basal medium plus phenol, cresol, sodium formate, sodium oxalate or sodium salicylate.

Under the test conditions of Shirling and Gottlieb (Shirling, E. B., and D. Gottlieb, 1966, Methods for characteization of Streptomyces species, Int. J. Syst.

Bacteriol. 16:313–340), growth was good on the negative control (basal medium only). On the basal medium with added compounds, growth was good on the positive control (D-glucose), D-xylose, and inositol; moderate on L-arabinose, sucrose, D-fructose, rhamnose, and raffinose. There was no growth on D-mannitol and cellulose.

Whole Cell Analysis. Cells were grown in tryptoneyeast extract broth (Dietz, A., 1967, *Streptomyces steffisburgensis* sp. n. J. Bacteriol. 94:2022–2026; and Shirling, E. B., and D. Gottlieb, supra) for 72 hours. meso-Diaminopimelic acid (meso-DAP) was detected as a major cell wall component putting this organism in the Cell Wall Type III classification. The whole cell sugar pattern analysis showed madurose and mannose.

Cultural and Biochemical Characteristics: See Table 3.

TABLE 1

Appearance of *Sebekia benihana* on Ektachrome

| Agar Medium | Surface Color | Reverse Color |
|---|---|---|
| Bennett's | Red-tan | Red-tan |
| Czapek's sucrose | Colorless | Colorless |
| Maltose-tryptone | Red-tan | Red-tan |
| Peptone-iron | Red-tan | Yellow-tan |
| 0.1% Tyrosine | Red | Red-tan |
| Casein starch | Trace pink | Pale pink-red |

TABLE 2

Reference color characteristics of *Sebekia benihana*

| | | ISCC-NBS color name charts illustrated with centroid colors* | | |
|---|---|---|---|---|
| Agar Medium | Determination | Chip No. | | Color |
| Bennett's | S | 29 | m. y Pink | Moderate yellowish pink |
| | to | 32 | gy. y Pink | Grayish yellowish pink |
| | R | 39 | gy. r O | Grayish reddish orange |
| | P | 33 | br Pink | Brownish pink |
| Czapek's sucrose | S | 9 | pk White | Pinkish white |
| | R | 9 | pk White | Pinkish white |
| | P | — | — | — |
| Maltose-tryptone | S | 29 | m. y Pink | Moderate yellowish pink |
| | to | 32 | gy. y Pink | Grayish yellowish pink |
| | R | 39 | gy. r O | Grayish reddish orange |
| | P | 33 | br Pink | Brownish pink |
| Hickey-Tresner** | S | 32 | gy. y Pink | Grayish yellowish pink |
| | R | 39 | gy. r O | Grayish reddish orange |
| | P | 33 | br Pink | Brownish pink |
| Yeast Extract-malt extract (ISP-2) | S | 19 | gy. Red | Grayish red |
| | R | 20 | d. gy. Red | Dark grayish red |
| | P | 33 | br Pink | Brownish pink |
| Oatmeal (ISP-3) | S | 45 | l. gy. r Br | Light grayish reddish brown |
| | R | 53 | m. O | Moderate orange |
| | P | 57 | l. Br | Light brown |
| Inorganic-salts starch (ISP-4) | S | 89 | p. Y | Pale yellow |
| | R | 89 | p. Y | Pale yellow |
| | P | — | — | — |
| Glycerol-asparagine (ISP-5) | S | 73 | p. OY | Pale orange yellow |
| | R | 73 | p. OY | Pale orange yellow |
| | P | — | — | — |
| S = Surface | | R = Reverse | | P = Pigment |

*Kelly, K. L., and D. B. Judd, 1955, The ISCC-NBS method of designating colors and a dictionary of color names, U.S. Dept. Comm. Circ. 553.
**Hickey, R. J. and H. D. Tresner, 1952, A cobalt-containing medium for sporulation of Streptomyces species, J. Bacteriol., 64:891-892.

TABLE 3

Cultural and biochemical characteristics of *Sebekia benihana*

| | Medium | Surface | Reverse | Other Characteristics |
|---|---|---|---|---|
| | Peptone-iron | Wrinkled orange (V) | Pale orange | Pale tan pigment<br>Melanin negative |
| | Calcium malate | Pale tan (V) | Pale tan | No pigment<br>Malate not solubilized |
| | Glucose asparagine | Pale tan (V) | Pale tan | Very pale tan pigment |
| | Skim Milk | Dark orange (V) | Orange | Pale tan pigment<br>Casein solubilized under growth |
| Agar | Tyrosine | Red-tan | Red-tan | Red-tan pigment<br>Tyrosine solubilized |
| | Xanthine | Orange (V) | Orange | Pale tan<br>Xanthine not solubilized |
| | Nutrient starch | Orange (V) | Muddy orange | No pigment |
| | Yeast extract-malt extract | Raspberry (V) with trace pink aerial | Maroon | Pale pink-tan pigment |
| | Peptone-yeast extract-iron (ISP-6) | Pale orange (V) | Pale orange-tan | Pale orange-tan pigment<br>Melanin negative |

TABLE 3-continued

Cultural and biochemical characteristics of Sebekia benihana

| Medium | | Surface | Reverse | Other Characteristics |
|---|---|---|---|---|
| | Tyrosine (ISP-7) | Pale peach aerial with raised red (V) | Peach to red | No pigment<br>Melanin negative |
| Gelatin | Plain<br>Nutrient | Colorless (V)<br>Colorless surface ring | —<br>— | No liquefaction<br>No liquefaction |
| Broth | Synthetic nitrate | Trace colorless pellicle | — | Compact colorless bottom growth<br>Nitrate not reduced |
| | Nutrient nitrate | — | — | Compact colorless bottom growth<br>Nitrate not reduced |
| | Litmus milk | — | — | No change<br>pH same as control (6.4) |

(V) = Vegetative growth

The novel microorganism used in the present invention is *Sebekia benihana*. One of its characteristics is the hydroxylation of the trans methyl group of the 3-methyl-2-butenyl side chain of ring A of novobiocin (I). A culture of this living microorganism can be obtained upon request from the permanent collection of the Northern Regional Research Center, Agricultural Research Services, U.S. Department of Agriculture, Peoria, Ill., U.S.A. The accession number of this culture is NRRL 11,111.

The microorganism is maintained on agar slants of various compositions (oatmeal agar, Hickey-Tresner Agar, TYG-agar), stored at 4° and transferred monthly as is well known to those skilled in the art. It is preferred that the microorganism be maintained on agar of the following composition: tryptone (0.5%), yeast extract (0.3%), glucose (2.0%), sodium phosphate monobasic (0.1%) magnesium sulfate (0.02%), ferrous sulfate (0.002%), and agar (2%), adjusted to pH 7.2, in deionized water.

For the purpose of this invention, the microorganism is grown in or on a sterile medium favorable to its development. Sources of nitrogen and carbon are present in the culture medium, the pH is properly adjusted and an adequate sterile air supply is maintained as is well known to those skilled in the art.

Nitrogen in an assimilable form is provided by sources normally employed in fermentations which are well known to those skilled in the art, such as corn steep liquor, cottonseed meal, soy bean meal, yeast extracts, Torula yeast, peptone, tryptone, soluble and insoluble vegetable or animal protein, lactalbumin, casein, whey, distillers' solubles, amino acids, nitrates, and ammonium compounds such as ammonium tartrate, nitrate, sulfate, and the like.

Available carbon is provided by sources normally used in fermentations which are well known to those skilled in the art, such as glucose, fructose, sucrose, galactose, maltose, dextrin, meat extracts, peptones, amino acids, proteins, fatty acids, glycerol, sodium lactate, whey and the like. These materials are used either in a purified state or as whey concentrate, corn steep liquor, grain mashes, cottonseed meal and the like or as mixtures of the above. Many of the above sources of carbon may also serve as a source of nitrogen.

The medium may also contain naturally present or added mineral constituents such as calcium, copper, iron, potassium, phosphorus, magnesium and the like, such as potassium phosphate, calcium chloride, ferrous sulfate and magnesium sulfate.

In addition, the medium may contain yeast extract which supplies a variety of nutrients including vitamins useful for growth of the microorganisms.

The preferred medium for the process of the present invention is TYG medium. It is utilized for the growth of the microorganism prior to addition of the substrate and during the bioconversion process. The composition of TYG medium is as follows:

| Ingredient | % |
|---|---|
| Tryptone | 0.5 |
| Yeast extract | 0.3 |
| Glucose | 2.0 |

TYG medium is adjusted to pH 7.2, in deionized water.

The concentrations of the three ingredients in TYG medium may vary somewhat without any problems as is well known to those skilled in the art.

The organism is grown by homogenizing a piece of the mycelium from an agar slant and adding a portion of the suspension to the growth medium (100 ml. in a 250 ml. Erlenmeyer flask). The organism is grown at a temperature of 20°-35°, 25°-28° being preferred. The organism is grown with shaking (100-500 rmp). Alternatively the flask may be aerated by bubbling air thru. The growth process takes about 2-4 days.

After a suitable period of growth, usually 3 days, (1) the substrate may be added for bioconversion, (2) a portion of the growth may be utilized to inoculate a number of small Erlenmeyer flasks, or (3) the total contents of the shaker flasks along with a number of other small flasks may be added to a larger fermentor. For instance, a fermentor containing 10 l. of fermentation medium may be seeded with the contents of 2-10 Erlenmeyer flasks (250 ml.) each containing 100 ml. of the inoculum. Uusually an antifoam agent such as UCON ® (1-5 ml.) is added to each fermentor of 10 l. capacity. During growth, the fermentation medium is stirred (100-400 rpm), aerated (1-5 l. air/min./10 l. fermentation medium) and maintained at 20°-35°, preferably 25°-28°. After a period of 2-4 days, usually 3 days, the contents of the 10 l. fermentor may be (1) used to inoculate a larger fermentor or (2) a novobiocin-type compound (I) may be added to the fermentor to undergo bioconversion.

The substrates which undergo bioconversion according to the process of the present invention, are novobiocin-type compounds of the formula:

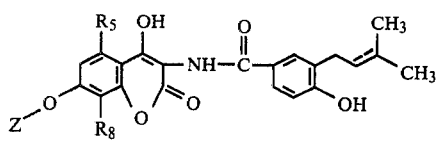

or salt thereof where $R_5$, $R_8$, Z and $=\!=\!=$ are defined supra.

The novobiocin-type compounds within the scope of formula I are either known to those skilled in the art or are readily prepared from known compounds by methods well known to those skilled in the art. For example novenamine can be N-acylated with various p-hydroxybenzoic acid analogs, see U.S. Pat. No. 3,890,297.

It is preferred that $R_5$ is hydrogen and $R_8$ is methyl or chlorine.

For novobiocin (U.S. Pat. No. 3,049,534) $R_5$ is hydrogen, $R_8$ is methyl, $=\!=\!=$ is a double bond and Z is

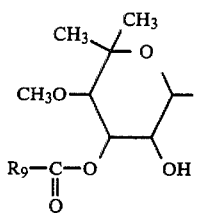

where $R_9$ is amino.

Dihydronovobiocin (U.S. Pat. No. 3,175,944) is identical to novobiocin except $=\!=\!=$ is a single bond.

Chlorobiocin (U.S. Pat. No. 3,682,886) is identical to novobiocin except $R_8$ is a chlorine atom and $R_9$ is 5-methylpyrrole.

Novobiocic acid [J. W. Hinman, et al. J.A.C.S. 79, 3789 (1957)] is identical to novobiocin except that Z is hydrogen.

Novobiocin, dihydronovobiocin, chlorobiocin, novobiocic acid and the other novobiocin-type compounds within the scope of formula I have at least 2 acidic protons. When Z is hydrogen there are at least 3 acidic protons. Therefore, when novobiocin-type compounds within the scope of formula I are reacted with dilute base such as 0.01–0.5 M sodium or potassium bicarbonate, salts are formed. With stronger bases such as 0.1–0.5 M sodium hydroxide, bis salts are formed except when Z is hydrogen, tris salts are formed.

The substrates, the novobiocin-type compounds (I), are added to the fermentation medium in their salt form in an aqueous solution. The substrate may be added to give a concentration of as low as 50 μg./ml. or as high as 1500 μg./ml. It is preferred that the concentration of (I) be 100–1000 μg./ml.

An alternative method of substrate addition is to dissolve the free acid form of nobobiocin-type compounds (I) in a minimal amount of an organic diluent such as alcohol, dimethylformamide, etc., for addition to the fermentation media. Another alternative method of substrate addition involves production of the substrate by fermentation and then adding a growing culture of Sebekia benihana to the fermentation. The Sebekia benihana culture may be added in the fermentation medium or as the centrifuged mycelium. This method, a two-step fermentation, produces hydroxynovobiocin (II) and hydroxychlorobiocin (II) from fermentations producing novobiocin (U.S. Pat. No. 3,049,534) and chlorobiocin (U.S. Pat. No. 3,682,886).

The bioconversion takes place at 20°–35°, preferably 25°–28°, with agitation (100–500 rpm) or stirring (100–400 rpm) and aeration either by surface contact in a shake flask or 1–5 l./min./10 l. fermentation medium in a fermentor.

As the bioconversion process proceeds, the reaction is monitored by TLC. A suitable TLC system is silica gel with ethyl acetate:methanol, 4:1. As the bioconversion takes place a more polar compound, the product (II), is formed at the expense of the substrate. The time necessary to obtain maximum yields from the bioconversion will range from 3 to greater than 10 days depending on the amount of mycelial growth, the temperature, the aeration, etc., but most importantly on the concentration of the substrate (I).

Following completion of the bioconversion, as measured by TLC, the products are recovered and purified by methods well known to those skilled in the art. The fermentation beer is adjusted to pH 2–5 with an acid such as hydrochloric, sulfuric, phosphoric, etc. The solids are separated by centrifugation or by mixing the fermentation beer with approximately 1/10 volume of a filter aid such as Dicalite ® 4,200, or any other diatomaceous earth product.

When using a filter aid the mixture is then filtered over a bed of the same filter aid. The cake is extracted with an organic aqueous immiscible diluent such as ethyl acetate, chloroform, carbon tetrachloride, benzene, toluene, methylene chloride, SSB or mixtures thereof. The filtrate is extracted with the same organic diluent as is used to extract the cake. The combined organic layers are washed with brine, dried with sodium sulfate or magnesium sulfate, filtered, and concentrated under vacuum with or without heat.

An alternative recovery process for the hydroxynovobiocins (II) is utilization of an anion exchange resin as is well known to those skilled in the art.

The recovery process usually yields an oil. This oil is dissolved in a minimal amount of an organic diluent such as listed above or mixtures thereof either alone or with small amounts of methanol, ethanol or acetone added. This mixture is added to a silica gel or alumina column utilizing the approximate ratios of 100 g. silica gel or 30 g. alumina/gram of oil. The column is developed with solvents well known to those skilled in the art. Gradient elution is preferable, utilizing solvent systems such as ethyl acetate: methanol, 10:1 or chloroform:acetone, 20:1. The fractions are assayed by TLC as described previously. Homogeneous (TLC) fractions corresponding to the more polar compound (lower Rf value) are pooled, and concentrated to give the hydroxynovobiocin (II).

An alternative procedure for purification of the oil is countercurrent distribution.

The hydroxynovobiocins (II) are identified by proton-NMR, UV, elemental analysis, C-13 NMR, IR, etc.

The hydroxynovobiocins (II) have antibiotic activity as demonstrated by the assay of L. J. Hanka, et al. in Antimicrobial Agents and Chemotherapy 1962, pp. 565-9.

The hydroxynovobiocins (II) are useful in the same manner and in the same way as the corresponding nobobiocin-type parent compounds (I), except that about 10 times higher concentration than novobiocin should be used, see U.S. Pat. Nos. 3,049,534; 3,175,944 and 3,682,886. The hydroxynovobiocin-type compounds (II) are useful to sterilize glassware and utensils in the concentration range of 0.01–10.0%. Walls, bench tops and floors may be cleaned of susceptible organisms using the same concentration range. In addition, the hydroxy novobiocin-type compounds can be used to selectively destroy susceptible organisms in soil samples prior to screening for antibiotics. Further these hydroxy compounds (II) may be used to destroy susceptible organisms in the bowels of animals for studies of digestion and excretion.

The hydroxynovobiocins (II) have 2 acidic protons and therefore form salts and bis-salts as described above. In the present invention pharmaceutically acceptable salts have the same utility as do the parent free acids.

Not all salts are pharmaceutically acceptable. Examples of pharmaceutically acceptable salts include those derived from the alkali metals, for example, sodium and potassium and alkaline earth metals, for example, calcium and magnesium, and amines, for example ammonia.

EXAMPLES

The invention may be more fully understood from the following examples which are illustrative of the process and compounds of the present invention but are not to be construed as limiting.

EXAMPLE 1

Bioconversion of novobiocin (I) to hydroxynovobiocin (II) (Formulas I and II: $R_5$ and $R_8$ are hydrogen; ==== is a double bond; Z is

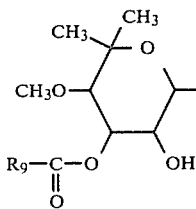

where $R_9$ is amino)

(a) The microorganism

*Sebekia benihana* is maintained on agar slants of the following composition: tryptone (0.5%), yeast extract (0.3%), glucose (2.0%), sodium phosphate monobasic (0.1%), magnesium sulfate (0.02%), ferrous sulfate (0.002%), and agar (2%) adjusted to pH 7.2. The agar slants are maintained at 4° and transferred monthly.

(b) Growth of the microorganism

A piece of the mycelium is removed from the agar slant, homogenized in sterile water (3 ml.) and inoculated into 100 ml. of the same sterile medium as was used for the agar slants without the agar in a 250 ml. Erlenmeyer flask.

The microorganism is incubated on a rotary shaker (300 rpm) at 25°–28°. After 2 days heavy mycelial growth occurs.

(c) The substrate

Novobiocin (U.S. Pat. No. 3,049,534) is dissolved in 0.1 M sodium bicarbonate. Novobiocin (10 mg.) is then added to the shake flask to give a concentration of novobiocin of 100 μg./ml. in the fermentation medium.

(d) Bioconversion

Following addition of the novobiocin the bioconversion takes place at 25°–28° at 300 rpm. During 3 days of bioconversion the substrate disappears with the simultaneous accumulation of a more polar product, hydroxynovobiocin (II), as measured by TLC on silica gel with ethyl acetate: methanol, 4:1. In this system novobiocin has an Rf of 0.46 and hydroxynovobiocin 0.24.

EXAMPLE 2

Bioconversion of novobiocin (I) to hydroxynovobiocin (II) (Formulas I and II: $R_5$ and $R_8$ are hydrogen; ==== is a double bond; Z is

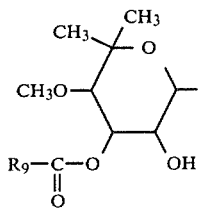

where $R_9$ is amino)

Following the general procedure of Example 1 and making minor non-critical variations, the fermentation is scaled up as set forth below.

Fifty Erlenmeyer flasks (500 ml.) containing sterile TYG medium (200 ml. each) are inoculated with 10 ml. of a 3 day old seed (5% inoculum). This medium is incubated for 2 days. Then novobiocin is added to a final concentration of 150 μg./ml. (a total of 1.5 g. of novobiocin) and incubated for 2 days. TLC shows the bioconversion is complete.

(e) Isolation

Hydrochloric acid is added to the fermentation beer (9 l., pH 7.6) to adjust to pH 5. The mixture is filtered over Dicalite ® 4,200. The cake is extracted with ethyl acetate (2 l.). The filtrate is extracted twice with ethyl acetate (3 l. each time). The organic layers are combined, washed with brine, dried over magnesium sulfate, filtered and concentrated under vacuum with mild heat to an oil.

(f) Purification

The oil is dissolved in ethyl acetate:methanol, (4 ml., 10:1) and placed on a silica gel column (2.5×100 cm.). Gradient elution is performed with ethyl acetate:methanol going from 9:1 to 3:1 at a flow rate of 7 ml./min. and collecting 25 ml. fractions.

Fractions which are homogeneous and which correspond to a compound which is more polar than the substrate (I) as measured by TLC, are pooled, and concentrated to give hydroxynovobiocin (130 mg.).

(g) Identification

Proton-NMR (1% TMS, $d_6$-DMSO) 1.1, 1.3, 1.7, 2.2, 3.2-3.7, 3.8, 4.1, 4.8-5.8, 6.6, 6.8-7.8 δ.

C-13 NMR (1% TMS, $d_6$-DMSO) 8.5, 13.8, 22.9, 27.8, 28.7, 61.1, 66.5, 69.1, 70.6, 78.0, 81.1, 98.8, 99.5, 108.8, 112.0, 114.4, 115.7, 122.0, 123.0, 125.2, 127.0, 127.3, 130.0, 135.8, 151.4, 156.1, 156.5, 158.2, 162.2, 166.6, and 167.2 δ.

EXAMPLE 3

Bioconversion of novobiocin (I) to hydroxynovobiocin (II) (Formulas I and II: $R_5$ and $R_8$ are hydrogen; ==== is a double bond; Z is

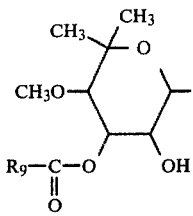

where $R_9$ is amino)

Following the general procedure of Examples 1 and 2, and making minor non-critical variations the substrate concentration is increased from 100 and 150 μg./ml. to 750 μg./ml. and the bioconversion time extended to 10 days, the product is hydroxynovobiocin.

EXAMPLE 4

Bioconversion of chlorobiocin (I) to hydroxychlorobiocin (II) (Formulas I and II: $R_5$ is hydrogen; $R_8$ is chlorine; ==== is a double bond; Z is

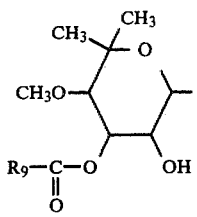

where $R_9$ is 5-methylpyrryl)

Following the general procedure of Examples 1 and 2, but substituting chlorobiocin (U.S. Pat. No. 3,682,886) for novobiocin, incubating the substrate with the culture for 5 days rather than 3 days and making other minor noncritical variations, hydroxychlorobiocin is obtained.

EXAMPLE 5

Bioconversion of dihydronovobiocin (I) to hydroxydihydronovobiocin (II) (Formulas I and II: $R_5$ and $R_8$ are hydrogen; ==== is a single bond; Z is

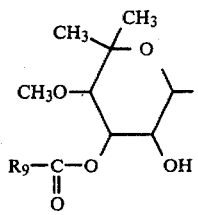

where $R_9$ is amino)

Following the general procedure of Examples 1 and 2, but substituting dihydronovobiocin (U.S. Patent 3,175,944) for novobiocin and making other minor noncritical variations, hydroxydihydronovobiocin is obtained.

EXAMPLE 6

Bioconversion of novobiocic acid (I) to hydroxynovobiocic acid (II) (Formulas I and II: $R_5$ and $R_8$ are hydrogen; ==== is a double bond; Z is hydrogen)

Following the general procedure of Examples 1, 2, and 3 but substituting novobiocic acid, J.A.C.S., 79, 3789 (1957), for novobiocin and making other minor non-critical variations, the bioconversion produces hydroxynovobiocic acid.

Upon completion of the bioconversion the fermentation medium has a pH 8.5. Hydrochloric acid is added to pH 3. The mixture is filtered over Dicalite ® 4,200. The Dicalite ® is washed with acetone to remove water and product. The acetone is stripped off, both the filtrate and aqueous wash are extracted with ethyl acetate. The combined extracts are dried over sodium sulfate, filtered and concentrated to a solid.

The solid material is dissolved in a minimal amount of ethyl acetate and placed on a high performance liquid chromatography silica gel column (2.5 cm.×100 cm.). The column is eluted with ethyl acetate at a flow rate of 4 ml./min., 24 ml. fractions are collected. Fractions which are homogenous by TLC with an RF corresponding to a compound more polar than the substrate are pooled, and concentrated to give hydroxynovobiocic acid (500 mg.).

Analysis:
Calc'd. for $C_{22}H_{21}NO_3$: C, 64.20; H, 5.12; N, 3.41.
Found: C, 63.59; H, 5.06; N, 3.42.
Mass spectrum m/e-411; proton-NMR (1% TMS, d$_6$DMSO) 1.7, 2.2, 2.5, 3.3, 3.9, 6.8, 6.9, 7.5, 7.7, 7.8, 9.1, 10.1, and 10.4 δ.

EXAMPLE 7

Hydroxynovobiocin by two-step fermentation

Following the general procedure of U.S. Pat. No. 3,049,534 novobiocin is produced by fermentation. When the production of novobiocin is maximal and ready for recovery, a growing culture of *Sebekia benihana* in an aqueous nutrient media is added, and the mixture is stirred or agitated and aerated as described in Examples 1 and 2 until TLC shows the bioconversion of novobiocin to hydroxynovobiocin is complete. The hydroxynovobiocin is recovered and purified according to the procedure of Example 2.

EXAMPLE 8

Hydroxychlorobiocin by two-step fermentation

Following the general procedure of U.S. Pat. No. 3,682,886 chlorobiocin is produced by fermentation. When the production of chlorobiocin is maximum and ready for recovery a growing culture of *Sebekia benihana* in an aqueous nutrient medium is added and the mixture stirred or agitated and aerated as described in Examples 1 and 2 until TLC shows the bioconversion of chlorobiocin to hydroxychlorobiocin is complete. Hydroxychlorobiocin is recovered and purified according to the process of Example 2.

The definitions and explanations below are for the terms as used throughout the entire patent application including both the specification and claims.

DAP refers to diaminopimelic acid.
ISP refers to International Streptomycetes Project.
SEM refers to scanning election microscope.
TEM refers to transmission election microscope.

We claim:
1. A process for preparing a hydroxynovobiocin-type compound of the formula:

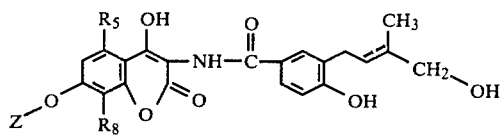

or pharmaceutically acceptable salt thereof which comprises (1) cultivating Sebekia benihana having the identifying characteristics of NRRL 11,111 and novobiocin-hydroxylating mutants thereof in an aqueous nutrient medium under aerobic conditions;

(2) contacting a novobiocin-type compound of the formula:

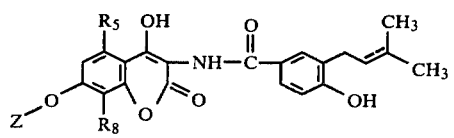

with the Sebekia benihana culture in an aqueous nutrient medium under aerobic conditions at 20°–35° and;

(3) recovering the hydroxynovobiocin-type compound (II) where $R_5$ an $R_8$ may be the same or different and are hydrogen, alkyl of 1 thru 5 carbon atoms, halogen, nitro, cyano, carboxyl or —N-$R_\alpha R_\beta$ where $R_\alpha$ and $R_\beta$ may be the same or different and are hydrogen or alkyl of 1 thru 5 carbon atoms; ---- is a single or double bond and Z is hydrogen or

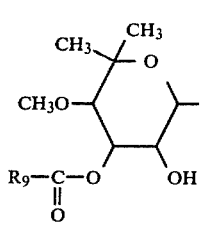

where $R_9$ is amino, 2-pyrryl, -2-(5-methyl)-pyrryl, 2-furyl, and 2-(5-methyl)-furyl.

2. A process according to claim 1 where the novobiocin-type compound (I) is novobiocin.

3. A process according to claim 1 where the novobiocin-type compound (I) is dihydronovobiocin.

4. A process according to claim 1 where the novobiocin-type compound (I) is chlorobiocin.

5. A process according to claim 1 where the novobiocin-type compound (I) is novobiocic acid.

6. A process for producing hydroxynovobiocin of the formula:

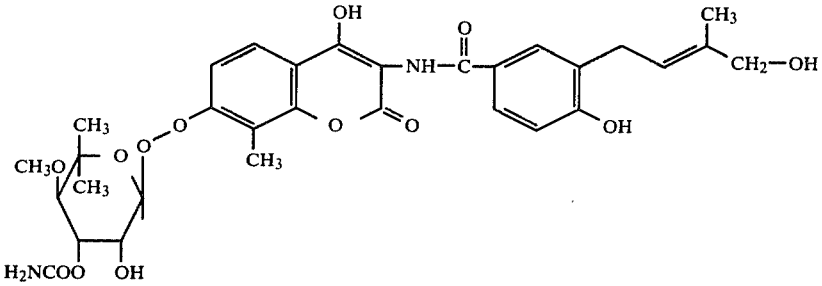

which comprises (1) producing novobiocin by fermentation;

(2) contacting a growing culture of *Sebekia benihana* having the identifying characteristics of NRRL 11,111 and novobiocin-hydroxylating mutants thereof in an aqueous nutrient media under aerobic conditions at 20°–35° with the fermentation and;

(3) recovering the hydroxynovobiocin.

7. A process for producing hydroxychlorobiocin of the formula:

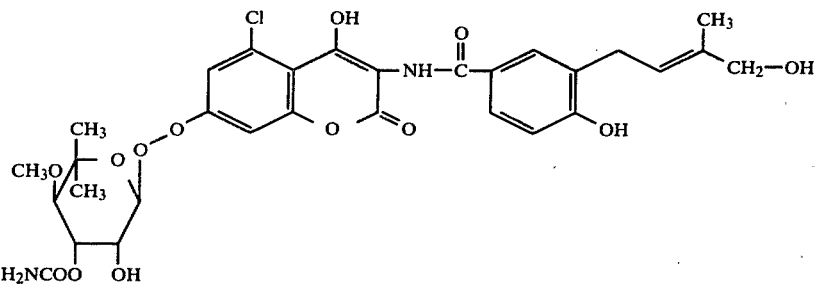

which comprises (1) producing chlorobiocin by fermentation;

(2) contacting a growing culture of Sebekia benihana having the identifying characteristics of NRRL 11,111 and novobiocin-hydroxylating mutants thereof in an aqueous nutrient media under aerobic conditions at 20°–35° with the fermentation and;

(3) recovering the hydroxychlorobiocin.

8. A biologically pure culture of the microorganism Sebekia benihana, having identifying characteristics of NRRL 11,111, the culture being capable of producing hydroxy novobiocin-type compounds

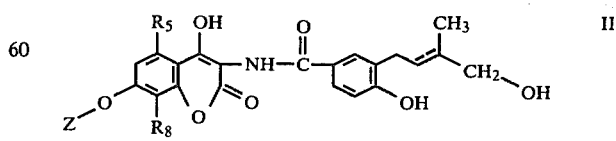

in a recoverable quantity upon fermentation of a novobiocin-type compound (I) in an aqueous nutrient medium where $R_5$, $R_8$, ---- and Z are defined in claim 1.

* * * * *